United States Patent
Dotan et al.

(10) Patent No.: US 9,872,497 B2
(45) Date of Patent: Jan. 23, 2018

(54) PEST CONTROL MIXTURE

(71) Applicant: ADAMA MAKHTESHIM LTD., Beer-Sheva (IL)

(72) Inventors: Assaf Dotan, Kfar-Varburg (IL); Tamar Danon, Ramat-Gan (IL)

(73) Assignee: MAKHTESHIM CHEMICAL WORKS LTD., Beer Sheva (IL)

( * ) Notice: Subject to any disclaimer, the term of this patent is extended or adjusted under 35 U.S.C. 154(b) by 0 days.

(21) Appl. No.: 14/438,296

(22) PCT Filed: Nov. 5, 2013

(86) PCT No.: PCT/IL2013/050909
§ 371 (c)(1),
(2) Date: Apr. 24, 2015

(87) PCT Pub. No.: WO2014/072970
PCT Pub. Date: May 15, 2014

(65) Prior Publication Data
US 2015/0250182 A1    Sep. 10, 2015

Related U.S. Application Data

(60) Provisional application No. 61/723,036, filed on Nov. 6, 2012.

(51) Int. Cl.
| | |
|---|---|
| *A61K 31/70* | (2006.01) |
| *A01N 43/04* | (2006.01) |
| *A01N 47/34* | (2006.01) |
| *A01N 43/22* | (2006.01) |
| *A01N 37/44* | (2006.01) |
| *A01N 43/40* | (2006.01) |
| *B65D 81/32* | (2006.01) |

(52) U.S. Cl.
CPC ............ *A01N 47/34* (2013.01); *A01N 37/44* (2013.01); *A01N 43/22* (2013.01); *A01N 43/40* (2013.01); *B65D 81/32* (2013.01)

(58) Field of Classification Search
CPC ........ A01N 37/44; A01N 43/22; A01N 43/40; A01N 47/34; B65D 81/32
USPC ................................... 514/28; 206/232, 568
See application file for complete search history.

(56) References Cited

U.S. PATENT DOCUMENTS

| | | | |
|---|---|---|---|
| 6,001,981 A | 12/1999 | Deamicis et al. | |
| 6,444,667 B1 | 9/2002 | Andersch et al. | |
| 6,686,387 B2 | 2/2004 | Andersch et al. | |
| 9,125,416 B2 * | 9/2015 | Pohlman | A01N 43/90 |
| 2006/0211655 A1 | 9/2006 | Mencke et al. | |
| 2011/0033432 A1 | 2/2011 | Davies et al. | |
| 2011/0275583 A1 * | 11/2011 | Bretschneider | A01N 43/78 514/30 |
| 2012/0083463 A1 * | 4/2012 | Maue | A01N 43/40 514/30 |

FOREIGN PATENT DOCUMENTS

| | | |
|---|---|---|
| CN | 102342291 A | 2/2012 |
| CN | 102487955 A | 6/2012 |
| EP | 2476313 A1 | 7/2012 |
| WO | 2010023171 A2 | 3/2010 |
| WO | 2010030501 A2 | 3/2010 |
| WO | 2010052129 A2 | 5/2010 |
| WO | 2010076782 A2 | 7/2010 |
| WO | 2010149370 A1 | 12/2010 |
| WO | 2012053658 A2 | 4/2012 |
| WO | WO 2012053658 A2 * | 4/2012 ............. A01N 43/40 |

OTHER PUBLICATIONS

Darriet, Frederic and Corbel, Vincent, "Laboratory Evaluation of Pyriproxyfen and Spinosad, Alone and in Combination, Against Aedes aegypti Larvae", Journal of Medical Entomology, 43(6), 1190-1194, Nov. 2006.
Darriet, Frederic, et al., "Field Evaluation of pyriproxyfen and spinosad mixture for the control of insecticide resistant Aedes aegypti in Martinique (French West Indies)", Parasites & Vectors, 3(88), 8 pages, 2010.
PCT Third Party Observation submitted on Dec. 17, 2014 for PCT/ILI2013/050909.
Willmott, Amy, et al., "Efficacy of Pesticide Mixtures Against the Western Flower Thrips (Thysanoptera: Thripidae) Under Laboratory and Greenhouse Conditions", Journal of Economic Entomology, 106 (1), 247-256 (2013).
International Search Report and Written Opinion for PCT/IL2013/050909 dated Mar. 3, 2014, 10 pages.
English Translation of CN Office Action for CN Application No. 201380069573.3; International Filing Date Nov. 5, 2013; Office Action dated Feb. 1, 2016; 10 pages.
English Translation of CN Search Report for CN Application No. 201380069573.3; International Filing Date Nov. 5, 2013; dated Jan. 22, 2016; 3 pages.
Second Office Action for CN Application No. 201380069573.3; dated Dec. 8, 2016; 17 pages.

\* cited by examiner

*Primary Examiner* — My-Chau T Tran
(74) *Attorney, Agent, or Firm* — Cantor Colburn LLP

(57) ABSTRACT

A pesticidal mixture including (a) spinetoram; and (b) a compound of group A selected from novaluron, pyriproxyfen, tau-fluvalinate, and a combination thereof.

12 Claims, No Drawings

PEST CONTROL MIXTURE

This application is a national stage application of PCT/IL2013/050909, filed Nov. 5, 2013, which claims priority to U.S. Provisional Application Ser. No. 61/723,036, filed Nov. 6, 2012, which are hereby incorporated by reference in their entirety.

FIELD OF THE INVENTION

The present disclosure relates to a pesticidal mixture for pest control.

BACKGROUND OF THE INVENTION

Active agent mixtures are described in the literature. However, the control over the pests does not always satisfy the needs of agriculture practice. Additionally, the efficacy of mixtures are not entirely satisfactory in areas of pest control and/or toxicological and/or environmental effects.

Spinetoram is a semi-synthetic spinosyn. Spinetoram is a mixture of 50-90% (2R,3aR,5aR,5bS,9S,13S,14R,16aS,16bR)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,4,5,5a,5b,6,9,10,11,12,13,14,16a,16b-hexadecahydro-14-methyl-1H-as-indaceno[3,2-d]oxacyclododecine-7,15-dione and 50-10% (2S,3aR,5aS,5bS,9S,13S,14R,16aS,16bS)-2-(6-deoxy-3-O-ethyl-2,4-di-O-methyl-α-L-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione.

Spinetoram has been described in U.S. Pat. No. 6,001,981. Spinetoram is also described in The E-Pesticide Manual (Version 5.0.1, 2010, 15th Edition, Editor: C D S Tomlin)), Entry number 783.

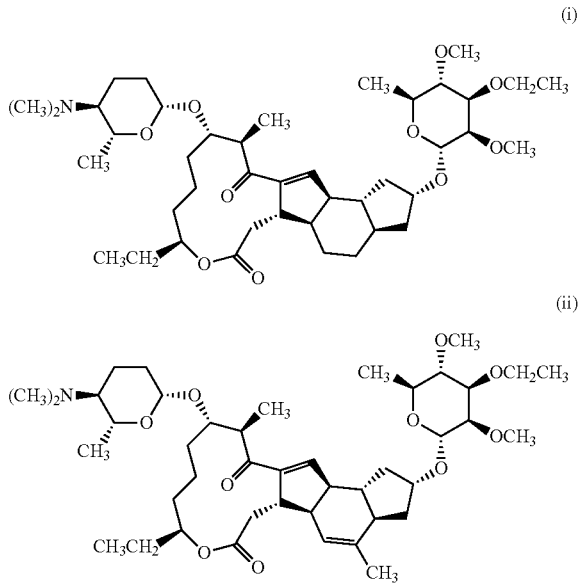

Spinetoram: Mixture of 50-90% component (i); and 50-10% component (ii).

Pesticidal mixtures comprising spinosyns have been described in WO 2010/052129, WO2010/030501, U.S. Pat. Nos. 6,444,667, 6,686,387 and US2006/0211655.

Pesticidal compositions and mixtures do not exert a satisfactory controlling effect in some cases, and therefore, there is still a need for development of new pesticidal mixtures having a satisfactory controlling effect.

Thus, it will be highly advantageous to have new pesticidal mixture combinations of spinetoram with various pesticides described in the invention, having a very good controlling effect on various pests, improving control over the pests, broadening the spectrum of control, and/or maintaining favorable and reduced environmental or toxicological effects.

SUMMARY OF THE INVENTION

According to one aspect there is provided a pesticidal mixture comprising (a) spinetoram; and (b) a compound of group A selected from novaluron. pyriproxyfen, tau-fluvalinate, and a combination thereof.

According to another aspect there is provided a pesticidal composition comprising a pesticidal mixture comprising (a) spinetoram.; and (b) a compound of group A selected from novaluron, pyriproxyfen, tau-fluvalinate, and a combination thereof; and an agriculturally acceptable carrier.

According to additional aspect there is provided a method for controlling pests in a crop, comprising contacting the pests or a locus, where control of the pest is desired, with a pesticidal mixture comprising (a) spinetoram; and (b) a compound of group A selected from novaluron, pyriproxyfen, tau-fluvalinate, and a combination thereof.

According to further aspect there is provided a kit comprising (a) at least one container including spinetoram; (b) at least one container including a compound of group A selected from novaluron, pyriproxyfen, tau-fluvalinate, and a combination thereof; and (c) instructions for applying said spinetoram and said compound of group A onto a pest or a locus, where control of the pest is desired.

According to still further aspect there is provided a kit comprising (a) at least one container including (i) spinetoram; and (ii) a compound of group A selected from novaluron, pyriproxyfen, tau-fluvalinate, and a combination thereof; and (b) instructions for applying said spinetoram and said a compound of group A onto a pest or a locus, where control of the pest is desired.

DETAILED DESCRIPTION OF THE INVENTION

Prior to setting forth the invention in detail, it may be helpful to provide definitions of certain terms to be used herein. Unless defined otherwise, all technical and scientific terms used herein have the same meaning as is commonly understood by one of skill in the art to which this invention belongs.

The use of the terms "a" and "an" and "the" and similar referents in the context of describing the invention (especially in the context of the following claims) are to be construed to cover both the singular and the plural, unless otherwise indicated herein or clearly contradicted by context.

As used herein the term "crop" includes reference to whole plant, plant organ (e.g., leaves, stems, twigs, roots, trunks, limbs, shoots, fruits etc.), or plant cells.

As used herein the term "propagation material" is to he understood to denote all the generative parts of the plant such as seeds and spores, vegetative structures such as bulbs, corms, tubers, rhizomes, roots stems, basal shoots, stolons, and buds.

According to one aspect there is provided a pesticidal mixture comprising (a) spinetoram; and (b) a compound of group A selected from novaluron, pyriproxyfen, tau-fluvalinate, and a combination thereof.

Spinetoram is a mixture of 50-90% (2R,3aR,5aR,5bS,9S,13S,14R,16aS,16bR)-2-(6-deoxy-3-O-ethyl-2,4-di-O-methyl-α-L-mannopyranosyloxy)-13-[2R,5S,6R)-5-(dimethylamino)tetrahydro-6-methylpyran-2-yloxy]-9-ethyl-2,3,3a4,5,5a,5b,6,9,10,11,12,13,14,16a,16b-hexadecahydro-14-methyl-1H-as-indaceno[3,2-d]oxacyclododecine-7,15-dione and 50-10% (2S,3aR,5aS,5bS,9S,13S,14R,16aS,16bS)-2-(6-deoxy-3-O-ethyl-2,4-di-O-methyl-α-t-mannopyranosyloxy)-13-[(2R,5S,6R)-5-(dimethylamino)tetrahydro-6-methylpyran-2-yloxy]-9-ethyl-2,3,3a,5a,5b,6,9,10,11,12,13,14,16a,16b-tetradecahydro-4,14-dimethyl-1H-as-indaceno[3,2-d]oxacyclododecine-7,15-dione.

Spinetoram is described in The E-Pesticide Manual (Version 5.0.1, 2010, 15th Edition, Editor: C D S Tomlin)), Entry number 783.

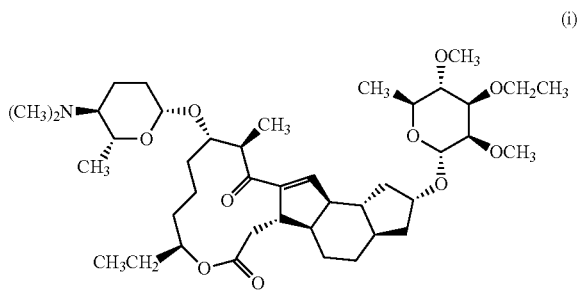

(i)

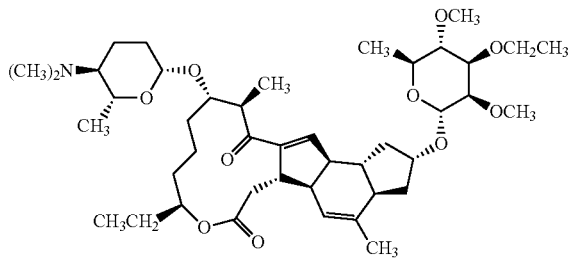

(ii)

Spinetoram; Mixture of 50-90% component 1); and 50-10% component (ii).

Novaluron ((±)-1-[3-chloro-4-(1,1,2-trifluoro-2-trifluoromethoxyethoxy)phenyl]-3-(2,6-difluorobenzoyl)urea),

is described in The E-Pesticide Manual (Version 5.0.1, 2010, 15th Edition, Editor: C D S Tomlin)), Entry number 621.

Tau-fluvalinate ((RS)-α-cyano-3-phenoxybenzyl N-(2-chloro-α,α,α-trifluoro-p-tolyl)-D-valinate),

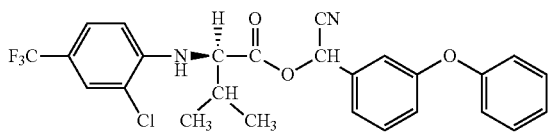

is described in The E-Pesticide Manual (Version 5.0.1, 2010, 15th Edition, Editor: C D S Tomlin)) Entry number 423, and Pyriproxyfen (4-phenoxyphenyl(RS)-2-(2-pyridyloxy)propyl ether)

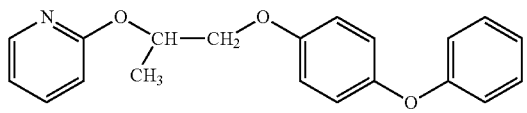 [SMILES: CC(COc1ccc(Oc2ccccc2)cc1)Oc1ccccn1]

is described in The E-Pesticide Manual (Version 5.0.1, 2010, 15th Edition, Editor: C D S Tomlin)) Entry number 749.

According to another aspect there is provided a pesticidal composition comprising a pesticidal mixture as described in the present disclosure; and an agriculturally acceptable carrier.

According to certain embodiments, the pesticidal mixture may result in a synergistic pesticidal activity when applied to pests.

Synergy can be calculated according to Colby S. R. in an article entitled "Calculating synergistic and antagonistic responses of herbicide combinations" published in the journal Weeds, 1967, 15, p. 20-22, incorporated herein by reference in its entirety.

A pesticidal composition comprising a mixture as described in the present disclosure may improve effectiveness of the pesticidal activity, may broaden the spectrum of control and/or allow minimizing the dosages of the active ingredients being used when compared to the use of such individual pesticides alone.

According to a specific embodiment the pest is selected from an insect, a mite, molluscs, or a combination thereof.

In a specific embodiment the pest is in an insect. In a specific embodiment the pest is in a mite. In a specific embodiment the pest is in a molluscs.

The term "pesticidal" especially relates to insecticidal and/or miticidal activities. The term "pesticidal" also refers to molluscicidal activity.

According to an additional aspect there is provided a synergistic pesticidal mixture comprising (a) spinetoram; and (b) a compound of group A selected from novaluron, pyriproxyfen, tau-fluvalinate, and a combination thereof.

According to an additional aspect there is provided a pesticidal composition comprising a pesticidal mixture as described in the present disclosure in a synergistically effective amount; and an agriculturally acceptable carrier.

The composition may be for use in controlling agricultural pests in a crop or a locus thereof comprising contacting the agricultural pests or the agricultural pests' food supply, habitat, breeding grounds, or locus with an effective amount of a mixture as described in the present disclosure.

According to a further aspect there is provided a method for controlling pests in a crop, comprising contacting the pests or a locus, where control of the pest is desired, with a pesticidal mixture comprising (a) spinetoram; and (b) a compound of group A selected from novaluron, pyriproxyfen, tau-fluvalinate, and a combination thereof.

According to a further aspect there is provided a method for controlling pests in a crop, comprising contacting the pests or a locus, where control of the pest is desired, with a composition comprising a pesticidal mixture as described in the present disclosure.

The locus may be the soil or water in which the crop is growing.

The disclosure additionally relates to a method for controlling pests in a crop or in a propagation material thereof, comprising contacting the pests or the agricultural pests' food supply, habitat, breeding grounds or locus with an amount of a combination of a pesticidal mixture as described in the present disclosure.

According to certain embodiments the ratio by weight of spinetoram and a compound of group A selected from novaluron, pyriproxyfen, tau-fluvalinate, and a combination thereof is from 1:1000 to 1000:1. In an embodiment the ratio by weight of spinetoram and a compound of group A is from 1:100 to 100:1. In a further embodiment the ratio by weight of spinetoram and a compound of group A is from 1:50 to 50:1. In still further embodiment the ratio by weight of spinetoram and a compound of group A is from 1:10 to 10:1. In an additional embodiment the ratio by weight of spinetoram and a compound of group A is from 1:8 to 8:1. In an additional embodiment the ratio by weight of spinetoram and a compound of group A is from 1:5 to 5:1.

According to some embodiments the ratio by weight of spinetoram and a compound of group A selected from novaluron, pyriproxyfen, tau-fluvalinate, and a combination thereof is 100:1 and below, 50:1 and below, 10:1 and below, 8:1 and below, 5:1 and below, 4:1 and below, 3:1 and below, 2:1 and below, 1.3:1 and below, 1:1 and below. According to some embodiments the ratio by weight of spinetoram and a compound of group A selected from novaluron, pyriproxyfen, tau-fluvalinate, and a combination thereof is 1:100 and above, 1:50 and above, 1:10 and above, 1:8 and above, 1:5 and above, 1:4 and above, 1:3 and above, 1:2 and above, 1:1.3 and above, 1:1 and above.

The ratio by weight of spinetoram and a compound of group A selected from novaluron, pyriproxyfen, tau-fluvalinate, and a combination thereof may be in a range between any of the above indicated values (e.g. 4:1 to 1:4, 4:1 to 1:3, 4:1 to 1:2, 4:1 to 1:1.3, 4:1 to 1:1, 3:1 to 1:4, etc.).

As used herein the terms "ha" refers to hectare.

According to certain embodiments, the application rates of spinetoram are from 0.5 gram per hectare ("g/ha") to 500 g/ha, specifically from 1 g/ha to 500 g/ha, specifically from 1 g/ha to 250 g/ha, more specifically from 1 g/ha. to 100 g/ha.

According to certain embodiments, the application rates of spinetoram are 0.5 g/ha and above, 1 g/ha and above, 1.5 g/ha and above, 2 g/ha and above, 2.5 g/ha and above, 3 g/ha and above, 3.5 g/ha and above, 4 g/ha and above, 4.5 g/ha and above, 5 g/ha and above, 5.5 g/ha and above, 6 g/ha and above.

According to certain embodiments, the application rates of spinetoram are 500 g/ha and below, 250 g/ha and below, 200 g/ha and below, 150 g/ha and below, 100 g/ha and below, 50 g/ha and below, 20 g/ha and below, 10 g/ha and below, 8 g/ha and below.

The application rate of spinetoram may be any range between any of the above indicated values.

According to certain embodiments, the application rates of a compound of group A are from 0.5 g/ha to 500 g/ha, specifically from 1 g/ha to 500 g/ha, specifically from 1 g/ha. to 250 g/ha, more specifically from 1 g/ha to 100 g/ha.

According to certain embodiments, the application rates of a compound of group A are 0.5 g/ha and above, 1 g/ha and above, 1.5 g/ha and above, 2 g/ha and above, 2.5 g/ha and above, 3 g/ha and above, 3.5 g/ha and above, 4 g/ha and above, 4.5 g/ha and above, 5 g/ha and above, 5.5 g/ha and above, 6 g/ha and above.

According to certain embodiments, the application rates of a compound of group A are 500 g/ha and below, 250 g/ha. and below, 200 g/ha and below, 150 g/ha and below, 100 g/ha and below, 50 g/ha and below, 20 g/ha and below, 10 g/ha and below, 8 g/ha and below.

The application rate of a compound of group A selected from novaluron, pyriproxyfen, tau-fluvalinate, may be any range between any of the above indicated values.

According to certain embodiments the application rates of the pesticidal mixture as described in the present disclosure are from 1 g/ha to 1000 g/ha. In a specific embodiment the application rates of the pesticidal mixture as described in the present disclosure are from 2 g/ha to 1000 g/ha.

In another embodiment, the application rates of the combination (mixture) of spinetoram and a compound of group A are from 1 g/ha to 500 g/ha. In yet another embodiment, the application rates of the combination of spinetoram and a compound of group A are from 1 g/ha to 250 g/ha. In yet another embodiment, the application rates of the combination of spinetoram and a compound of group A are from 1 g/ha to 200 g/ha. In yet another embodiment, the application rates of the combination of spinetoram and a compound of group A are from 1 g/ha to 150 g/ha. In yet another embodiment, the application rates of the combination of spinetoram and a compound of group A are from 1 g/ha to 100 g/ha. In yet another embodiment, the application rates of the combination of spinetoram and a compound of group A are from 1 g/ha to 50 g/ha. The above ranges refer to the application rates of a combination of spinetoram. and a compound of group A (namely a sum of the application rates of both active ingredients).

In an embodiment the spinetoram and the compound of group A are applied concomitantly or sequentially.

The application of spinetoram and the compound of group A may be in any desired order.

The term "applied sequentially" means the successive administration of a composition including spinetoram, and then administration of a composition of a compound of group A. When administered sequentially the spinetoram and the compound of group A are included in separate compositions. If the spinetoram and the compound of group A are administered sequentially, the order of administering thereof may be interchangeable.

The term "applied simultaneously" or "applied concomitantly" means administering the compounds substantially concurrently. These terms encompasses not only administering spinetoram and the compound of group A according to the invention in a single formulation (composition) but also the administration of each compound (i.e spinetoram and the compound of group A) in its own separate formulation. Where separate formulations are used, the compounds can be administered at essentially the same time, i.e., concurrently.

The application may be by any method known in the art, particularly, by methods such as by spraying, dipping, dusting, dressing, coating, and soaking.

The disclosure additionally relates to use of a composition comprising a pesticidal mixture as described in the present disclosure for controlling pests in a crop or locus thereof.

The disclosure further relates to a composition comprising a pesticidal mixture as described in the present disclosure for use in controlling pests in a crop or locus thereof. In a specific embodiment the pesticidal mixture is in a synergistic effective amount.

The crops include but not limited to vegetables, fruits, soybean, tobacco, cultivated mushrooms, cotton, oil seed rape, cereals, sunflower, peanuts, rice, corn, coffee, beans, peas, yucca, sugar cane, clover, spices, ornamentals, cocoa, beet.

In an embodiment, the crop may be vegetables, such as peppers, cabbage, broccoli, asparagus, artichoke, squash, lettuce, turnip, spinach, cauliflower, melon, watermelon, cucumbers, carrots, onions, garlic, cucurbits and potatoes; fruits for example, pome and stone fruits and berries, such as walnuts, kiwi, banana, avocado, olives, passion fruit, almonds, pineapples, apples, pears, plums, peaches, and cherries, tropical and subtropical fruits, table and wine grapes, citrus fruit, such as oranges, lemons, grapefruits and limes; cereals such as wheat, barley, rye, triticale, oats, sorghum; corn (maize) such as sweet corn; beet such as sugar beet, fodder beet; spices such as cardamom; ornamentals such as flowers, Christmas trees.

In another embodiment, the insect pests are of the order Coleoptera, such as *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass Ataenius), *Atomaria linearis* (pygmy mangold beetle). *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata*, *Cerosterna* spp, *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris*, *Conoderus stigmosus*, *Conotrachelus nenuphar* (plum curculio), *Cotinus nitidis* (Green June beetle). *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae*, *Hylobius pales* (pales weevil), *Hypera* spp. (weevils), *Hypera postica* (alfalfa weevil), *Hyperdoes* spp. (*Hyperodes* weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys futscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (Eurpoean chafer), *Rhynchophorus* spp. (weevils), *Scolytus* spp. (wood beetles), *Shenophorus* spp. (Billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle) and *Zabrus tenebioides*.

In yet another embodiment, the insect pests are of the order Diptera, such as *Aedes* spp. (mosquitoes) *Agromyza frontella* (alfalfa blotch leafminer), *Agromyza* spp. (leaf miner flies). *Anastrepha* spp. (fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranea fruit fly), *Chrysops* spp. (deer flies), *Cocliliamyia* spp. (screwworms), *Contarinia* spp. (Gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae, Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid *Musca autumnalis* (face fly), *Musca domestica* (house fly), *Oestrus ovis* (sheep bot fly), *Oscinella frit* (grass fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies) and *Tipula* spp. (crane flies).

In yet another embodiment, the insect pests are of the order Hemiptera, such as *Acrostemum hilare* (green stink bug), *Blissus leucopterus* (chinch bug), *Calocoris norvegicus* (potato mirid), *Cimex hemipterus* (tropical bed bug), *Cimex lectularius* (bed bug), *Dichelops melacanthus* (Dallas), *Dagbertus fasciatus, Dichelops furcatus, Dysdercus suturellus* (cotton stainer), *Edessa meditabunda, Eurygaster maura* (cereal bug), *Euschistus heros, Euschistus serous* (brown stink bug), *Helopeltis antonii, Helopeltis theivora* (tea blight plantbug), *Lagynotomus* spp. (stink bugs), *Leptocorisa oratorius, Leptocorisa varicomis, Lygus* spp. (plant bugs), *Lygus hesperus* (western tarnished plant bug), *Maconellicoccus hirsutus, Neurocolpus longirostris, Nezara viridula* (southern green stink bug), *Paratrioza cockerelli, Phytocoris* spp. (plant bugs), *Phytocoris califomicus, Phytocoris relativus, Piezodorus guildingi, Poecilocapsus lineatus* (fourlined plant bug), *Psallus vaccinicola, Pseudacysta perseae, Scaptocoris castanea* and *Triatoma* spp. (bloodsucking conenose bugs/kissing bugs).

In yet another embodiment, the insect pests are of the order Homoptera, such as *Acrythosiphon pisum* (pea aphid), *Adelges* spp. (adelgids), *Aleurodes proletella* (cabbage whitefly), *Aleurodicus disperses, Aleurothrixus floccosus* (woolly whitefly), *Aluacaspis* spp. *Amrasca bigutella bigutella, Aphrophora* spp. (leafhoppers), *Aonidiella aurantii* (California red scale), *Aphis* spp. (aphids), *Aphis gossypii* (cotton aphid), *Aphis fabae* (aphid), *Aphis pomi* (apple aphid), *Aulacorthum solani* (foxglove aphid), *Bemisia* spp. (whiteflies), *Bemisia argentifolii, Bemisia tabaci* (sweet potato whitefly), *Brachycolus noxius* (Russian aphid), *Brachycoryneila asparagi* (asparagus aphid), *Brevennia rehi, Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata, Metopolophiurn dirhodurn* (rose grain aphid), *Mictis longicornis, Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (banded wing whitefly), *Unaspis* spp. (scales), *Unaspis yanonensis* (arrowhead scale) and *Zulia entreriana*.

In yet another embodiment, the insect pests are of the order Lepidopter such as *Achoea Janata, Adoxophyes* spp., *Adoxophyes orana, Agrotis* spp. (cutworms), *Agrotis ipsilon* (black cutworm), *Alabama argillacea* (cotton leafworm), *Amorbia cuneana, Amyelosis transitella* (navel orangeworm), *Anacamptodes defectaria, Anarsia lineatella* (peach twig borer), *Anomis sabulifera* (jute looper), *Anticarsia gemmatalis* (velvetbean caterpillar), *Archips argyrospila* (fruittree leafroller) *Archips rosana* (rose leaf roller), *Argyrotaenia* spp. (tortricid moths), *Argyrotaenia citrine* (orange torrid), *Autograph gamma, Bongos crunodes, Bourbon cinnabar* (rice leaf folder), *Bucculatrix thurheriella* (cotton leafperforator), *Caloptilia* spp. (leaf miners), *Capua reticulana, Carposina niponensis* (peach fruit moth), *Chilo* spp., *Chlumetia transversa* (mango shoot borer), *Choristoneura rosaceana* (obliquebanded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Grapholita molesta* (oriental fruit moth), *Fledylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworin), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworin), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant *tortrix*), *Pandemis heparana* (brown apple *tortrix*), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis arena, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera littoralis* (cotton leafworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponometita* spp., *Zeuzera coffeae* (red branch borer) and *Zeuzera pyrina* (leopard moth).

In yet another embodiment, the insect pests are of the order Orthoptera, such as *Anabrus simplex* (Mormon cricket), *Gryllotalpidae* (mole crickets), *Locusta migratoria, Melanoplus* spp. (grasshoppers), *Microcentrum retinerve* (angularwinged katydid), *Pterophylla* spp. (kaydids), *chistocerca gregaria, Scudderia furcata* (forktailed bush katydid) and *Valanga nigricorni*.

In yet another embodiment, the insect pests are of the order Thysanoptera, such as *Frankliniella fusca* (tobacco *thrips*), *Frankliniella occidentalis* (western flower *thrips*), *Frankliniella shultzei Frankliniella williamsi* (corn *thrips*), *Heliothrips haemorrhaidalis* (greenhouse *thrips*), *Riphiphorothrips cruentatus, Scirtothrips* spp., *Scirtothrips citri* (citrus *thrips*), *Scirothrips dorsalis* (yellow tea *thrips*), *Taeniothrips rhopalantennalis* and *Thrips* spp.

The mites may be for example, Red Spider mite (*Tetranychus urticae*), European red mite (*Panonvchus ulmi*) Citrus Red mite (*Panonychus citri*) Rust Mite (*Aceria anthocoptes*), Citrus Flat mite (*Brevipalpus lewisi*), False Spider mite (*Brevipalpus phoenicis*), Yellow Mite (*Lorryia Formosa*), Brown Mite (*Bryobia rubrioculus*), Peach silver mite (*Aculus cornutus*), Two Spotted Spider mite (*Tetranychus urticae* Koch).

The Molluscs may be for example Grey garden slug (*Deroceras reticulatum*), Spanish slug (*Arion vulgaris*), Yellow slug (*Limax flavus*), Tree slug (*Limax marginatus*), Spanish Stealth slug (*Arion Flagellus*), Common Garden slug (*Arion distinctus*), Common Keeled slug (*Tandonia budapestensis*), Large Red slug and Black slug (*Arion ater*), Great grey slug (*Limax maximus*), Portuguese slug (*Arion lusitanicus*).

The application rates for the pesticidal compositions of spinetoram and a compound of group A can be influenced by many factors of the environment. The desired effect and can be determined under actual use conditions.

The composition may be applied in various mixtures or combinations of spinetoram and a compound of group A, for example in a single "ready-for-use" form, or in a combined spray mixture composed from separate formulations of the single active ingredients, such as a "tank-mix" form.

In certain embodiments, the composition is applied in the form of a ready-for-use formulation comprising spinetoram and a compound of group A. This formulation can be obtained by combining the mixture described in the present disclosure with an agriculturally acceptable carrier, a surfactant, or other application-promoting adjuvant customarily employed in formulation technology.

Compositions comprising (a) spinetoram and (b) a compound of group A may be employed in any conventional form, for example, in the form of a twin pack. The compositions may be in a form of, for example, an emulsion concentrates ("EC"), suspension concentrates ("SC"), soluble concentrates ("SL"), suspoemulsion ("SE"), oil dispersions ("OD"), water dispersible granules ("WDG" or "WG"), water soluble granules ("SG") and wettable powders ("WP"). Such compositions can be formulated using agriculturally acceptable carriers, surfactants or other application-promoting adjuvants customarily employed in formulation technology and formulation techniques that are known in the art.

In an embodiment, the amount of the active ingredient or ingredients in the composition is 0.01-99.9 percent by weight ("wt. %"), specifically 0.1-99 wt. %, more specifically 0.1-95 wt. %, even more specifically 0.1-90 wt. %, based on the total weight of the composition.

Examples of suitable solid carriers include mineral earths such as silica gels, silicates, talc, kaolin, attaclay, limestone, lime, chalk, bole, loess, clay, dolomite, diatomaceous earth, calcium sulfate, magnesium sulfate, magnesium oxide, sodium carbonate and bicarbonate, and sodium sulfate, ground synthetic materials, fertilizers, such as, for example, ammonium sulfate, ammonium phosphate, ammonium nitrate, ureas, and products of vegetable origin, such as cereal meal, tree bark meal, wood meal and nutshell meal, cellulose powders and other solid carriers.

Examples of suitable liquid carriers include water, alcohols such as methanol, cyclohexanol and decanol, ethylene glycol and polypropylene glycol, N,N-dimethylformamide, dimethylsulfoxide, N-alkylpyrrolidone, aromatic hydrocarbons such as alkylbenzenes and alkylnaphthalenes, paraffins, oils of olive, castor, linseed, tong, sesame, corn, peanut, cotton-seed, soybean, rape-seed and coconut, fatty acid esters, ketones such as cyclohexanone, 2-heptanone, isophorone and 4-hydroxy-4-methyl-2-pentanone and the like.

The term "surfactant," as used herein, means an agriculturally acceptable material which imparts emulsifiability, stability, spreading, wetting, dispersibility or other surface-modifying properties. Examples of suitable surfactants include non-ionic, anionic, cationic and ampholytic types such as lignin sulfonates, fatty acid sulfonates lauryl sulfonate), phosphate esters such as phosphate esters of alcohol alkoxylates, phosphate esters of alkylphenol alkoxylates and phosphate esters of styrylphenol ethoxylates, condensates of sulfonated naphthalene and naphthalene derivatives with formaldehyde, condensates of naphthalene or of naphthalenesulfonic acid with phenol and formaldehyde, alkylarylsulfonates, ethoxylated alkylphenols and aryl phenols, polyalkylene glycols and ethoxylated fatty alcohols.

Other ingredients, such as wetting agents, adhesives, thickeners, hinders, fertilizers or anti-freeze agents, may also be added to the composition including the combination of spinetoram and a compound of group A in order to increase the stability, density and viscosity of the composition.

In an embodiment, the combined amount of spinetoram and a compound of group A together in the ready-to-use formulations (compositions) is 0.1-99 wt. %.

In an embodiment, the combined amount of spinetoram and a compound of group A together in the ready-to-use formulations is 0.1-95 wt. %.

In another embodiment the amount of spinetoram and a compound of group A together in the ready-to-use formulations (compositions) is $10^{-4}$-99 wt. %, $10^{-3}$-99 wt. %, or $10^{-2}$-99 wt. In a specific embodiment the amount of spinetoram and a compound of group A together in the ready-to-use formulations (compositions) is $10^{-5}$-10 wt. %, $10^{-5}$-1 wt. %, $10^{-5}$-0.1 wt. %, $10^{-4}$-10 wt. %, $10^{-4}$-5 wt %, $10^{-4}$-2 wt %, $10^{-4}$-1 wt %, $10^{-4}$-0.5 wt %, or $10^{-4}$-0.1 wt %.

The remaining components in the formulation are for example t carrier and additives. In specific embodiment the carrier is aqueous based.

According to further aspect there is provided a kit comprising (a) at least one container including spinetoram; (b) at least one container including a compound of group A selected from novaluron, pyriproxyfen, tau-fluvalinate, and a combination thereof; and (c) instructions for applying said spinetoram and said compound of group A onto a pest or a locus, where control of the pest is desired.

In an embodiment the spinetoram and the compound of group A are applied concomitantly or sequentially.

According to still further aspect there is provided a kit comprising (a) at least one container including (i) spinetoram; and (ii) a compound of group A selected from novaluron, pyriproxyfen, tau-fluvalinate, and a combination thereof; and (b) instructions for applying said spinetoram and said compound of group A onto a pest or a locus, where control of the pest is desired.

The instructions may be in the form of printed matter, for example either as inserts or labels.

A synergistic effect exists wherever the action of a combination of active components is greater than the sum of the action of each of the components alone. Therefore, a synergistically effective amount (or an effective amount of a synergistic composition or combination) is an amount that exhibits greater pesticidal. activity than the sum of the pesticidal activities of the individual components.

In the field of agriculture, it is often understood that the term "synergy" is as defined by Colby S. R. in an article entitled "Calculating synergistic and antagonistic responses of herbicide combinations" published in the journal Weeds, 1967, 15, p. 20-22, incorporated herein by reference in its entirety. The action expected for a given combination of two active components can be calculated as follows:

$$E = X + Y - \frac{XY}{100}$$

in which E represents the expected percentage of pesticidal control for the combination of the two pesticides at defined doses (for example equal to x and y respectively), X is the percentage of pesticidal control observed by spinetoram at a defined dose (equal to x) and Y is the percentage of pesticidal control observed by a compound of group A at a defined dose (equal to y). When the percentage of pesticidal control observed for the combination is greater than the expected percentage, there is a synergistic effect.

It is appreciated that the spinetoram and the compound of group A, described in the invention in a particular aspect may be characterized by the various features, e.g., weight ratios, rates of applications etc., described in the present invention in the other aspects.

It is appreciated that one or more features, aspects, or embodiments of the present invention can be combined with one or more other features, aspects or embodiments of the present invention.

It is recognized that all embodiments of the invention, including those specifically described for different aspects of the invention, can be combined with any other embodiments of the invention as appropriate.

EXAMPLES

Example 1

Novaluron and Spinetoram in Control of *Plutella xylostella* on Cabbage (*Brassica oleracea* L Var. *Capitata*) and Broccoli (*Brassica oleracea* L Var. *Italica*)

Two trials—one on cabbage crops, and one on broccoli crops—were conducted in the district of La Plata (Buenos Aires, Argentina) with the goal of evaluating the efficacy of and interaction between foliar applications of Novaluron and Spinetoram in *Plutella* control. For preparation of the mixtures, Spinetoram (Delegate® 250 g a.i./Kg WG, Dow AgroSciences LLC) and Novaluron (Rimon® Supra 100 g a.i./Liter SC, Makhteshim Agan Group Company) were used. For each treatment in Examples 1-6 determined amounts of the formulated products were diluted with water to obtain a mixture.

Applications were made with a backpack-type sprayer fitted with a 2.1-m wide bar with nozzles set at 0.525 m from one another, with 8002 flat fan tips. In all cases, applications were made from 5 p.m. to 7 p.m. at a rate of 150 l·ha$^{-1}$ (Liter/ha).

Ten-meter-long plots were used, each divided into four ridges. Applications were made only on three ridges. A one-ridge-wide buffer zone was left among plots to minimize drift. Experiment design consisted in random blocks at four repetitions.

Evaluation following 1, 3 and 7 days post-application is presented in Table B below. Larvae per plant (LP) was an average of 10 plants per plot. 4 repetitions were averaged. % Efficacy of Control in Examples 1-6 was calculated, based on untreated control evaluated on the same days.

TABLE A

Description of each trial.

| | Location | Phenological Status | Rate of application (L/ha) |
|---|---|---|---|
| Trial 1 | Los Hornos (La Plata) | Vegetative | 150 lts/ha |
| Trial 2 | Etcheverry (La Plata) | Vegetative | 150 lts/ha |

TABLE B

Results

Trial 1 - Broccoli

| | | Novaluron | Spinetoram | % Efficacy of control | | |
|---|---|---|---|---|---|---|
| | | amount of ai$^{(*)}$, g/ha | amount of ai g/ha | 1 DAA | 3 DAA | 7 DAA |
| 1 | Novaluron + Spinetoram | 7.5 | 7.5 | 92.35% | 100.00% | 100.00% |
| 2 | Novaluron + Spinetoram | 7.5 | 5.625 | 86.47% | 100.00% | 100.00% |
| 3 | Novaluron + Spinetoram | 7.5 | 3.75 | 83.53% | 96.88% | 93.02% |
| 4 | Novaluron + Spinetoram | 7.5 | 1.875 | 64.71% | 78.13% | 100.00% |
| 5 | Novaluron + Spinetoram | 5.625 | 7.5 | 92.35% | 98.13% | 93.02% |
| 6 | Novaluron + Spinetoram | 5.625 | 5.625 | 79.41% | 100.00% | 93.02% |
| 7 | Novaluron + Spinetoram | 5.625 | 3.75 | 70.59% | 98.13% | 100.00% |
| 8 | Novaluron + Spinetoram | 5.625 | 1.875 | 57.06% | 93.75% | 100.00% |
| 9 | Novaluron + Spinetoram | 3.75 | 7.5 | 85.29% | 100.00% | 100.00% |
| 10 | Novaluron + Spinetoram | 3.75 | 5.625 | 80.59% | 91.88% | 93.02% |
| 11 | Novaluron + Spinetoram | 3.75 | 3.75 | 61.76% | 87.50% | 88.37% |
| 12 | Novaluron + Spinetoram | 3.75 | 1.875 | 54.12% | 75.00% | 93.02% |
| 13 | Novaluron + Spinetoram | 1.875 | 7.5 | 65.88% | 84.38% | 65.12% |
| 14 | Novaluron + Spinetoram | 1.875 | 5.625 | 64.71% | 76.25% | 93.02% |
| 15 | Novaluron + Spinetoram | 1.875 | 3.75 | 68.82% | 60.63% | 76.74% |
| 16 | Novaluron + Spinetoram | 1.875 | 1.875 | 41.18% | 65.63% | 76.74% |
| 17 | Novaluron | 7.5 | 0 | 47.06% | 59.38% | 88.37% |
| 18 | Spinetoram | 0 | 7.5 | 85.29% | 95.00% | 88.37% |
| 19 | Novaluron | 5.625 | 0 | 60.00% | 50.00% | 88.37% |
| 20 | Spinetoram | 0 | 5.625 | 62.94% | 82.50% | 81.40% |
| 21 | Novaluron | 3.75 | 0 | 60.00% | 53.13% | 76.74% |
| 22 | Spinetoram | 0 | 3.75 | 62.94% | 84.38% | 93.02% |
| 23 | Novaluron | 1.875 | 0 | 50.00% | 35.63% | 81.40% |

TABLE B-continued

| | | Results | | | |
|---|---|---|---|---|---|
| 24 Spinetoram | 0 | 1.875 | 41.18% | 54.38% | 46.51% |
| 25 Untreated controls (UTC) | 0 | 0 | 0.00% | 0.00% | 0.00% |

(*)In this table and tables below, the term "ai" refers to active ingredient.

Trial 2 - Cabbage

| | Novaluron amount of ai, g/ha | Spinetoram amount of ai, g/ha | % Efficacy of control | | |
|---|---|---|---|---|---|
| | | | 1 DAA | 3 DAA | 7 DAA |
| 1 Novaluron+ | 7.5 | 7.5 | 94.30% | 100.00% | 100.00% |
| 2 Novaluron+ | 7.5 | 5.625 | 87.45% | 100.00% | 100.00% |
| 3 Novaluron+ | 7.5 | 3.75 | 86.69% | 95.24% | 97.46% |
| 4 Novaluron+ | 7.5 | 1.875 | 69.58% | 83.33% | 95.76% |
| 5 Novaluron+ | 5.625 | 7.5 | 88.59% | 98.57% | 100.00% |
| 6 Novaluron+ | 5.625 | 5.625 | 85.55% | 96.19% | 100.00% |
| 7 Novaluron+ | 5.625 | 3.75 | 74.14% | 88.10% | 88.98% |
| 8 Novaluron+ | 5.625 | 1.875 | 75.29% | 83.33% | 88.98% |
| 9 Novaluron+ | 3.75 | 7.5 | 77.95% | 93.81% | 100.00% |
| 10 Novaluron+ | 3.75 | 5.625 | 80.99% | 85.71% | 93.22% |
| 11 Novaluron+ | 3.75 | 3.75 | 77.95% | 81.90% | 88.98% |
| 12 Novaluron+ | 3.75 | 1.875 | 61.98% | 73.81% | 70.34% |
| 13 Novaluron+ | 1.875 | 7.5 | 77.95% | 85.71% | 87.29% |
| 14 Novaluron+ | 1.875 | 5.625 | 71.48% | 80.95% | 83.05% |
| 15 Novaluron+ | 1.875 | 3.75 | 68.44% | 74.76% | 72.03% |
| 16 Novaluron+ | 1.875 | 1.875 | 62.74% | 52.38% | 55.08% |
| 17 Novaluron | 7.5 | 0 | 55.13% | 57.14% | 42.37% |
| 18 Spinetoram | 0 | 7.5 | 85.55% | 73.81% | 87.29% |
| 19 Novaluron | 5.625 | 0 | 70.34% | 52.38% | 59.32% |
| 20 Spinetoram | 0 | 5.625 | 72.24% | 78.57% | 100.00% |
| 21 Novaluron | 3.75 | 0 | 60.84% | 57.14% | 32.20% |
| 22 Spinetoram | 0 | 3.75 | 58.94% | 66.67% | 95.76% |
| 23 Novaluron | 1.875 | 0 | 63.88% | 58.10% | 8.47% |
| 24 Spinetoram | 0 | 1.875 | 67.68% | 59.52% | 83.05% |
| 25 Untreated controls (UTC) | 0 | 0 | 0.00% | 0.00% | 0.00% |

Example 2

Novaluron and Spinetoram in Fall Armyworm
(*Spodoptera frugiperda*) Control in Sweet Corn
(*Zea mays* Var. *Saccharata*)

Two trials were conducted on sweet corn crops in the district of Orán (Salta, Argentina) with the goal of evaluating the efficacy and interaction of foliar applications of Novaluron and Spinetoram on fall armyworms (*Spodoptera frugiperda*). For preparation of the mixtures the products used are as described in Example 1.

Applications were made with a backpack type sprayer fitted with a 2.1-m wide bar with nozzles set at 0.525 in from one another and fitted with 8002 flat fan tips. In all cases, applications were made between 6.00 p.m. and 9.00 p.m. at a rate of 205 l·ha$^{-1}$.

Ten-meter-long plots were used, each divided into four ridges. Applications were made only on three ridges. A one-ridge-wide buffer zone was left among plots to minimize drift. Experiment design consisted in random blocks at four repetitions.

The evaluation following 1, 3 and 7 days post-application is presented in Table B below. Larvae per plant (LP) was an average of 10 plants per plot (4 repetitions were averaged). % Efficacy was calculated in the same manner as described in Example 1.

TABLE A

Description of each trial

| | Location | Phenological Status | Rate of application (l · ha) |
|---|---|---|---|
| Trial 1 | Rio Blanco (Oran, Salta) | V 5 | 205 lts/ha |
| Trial 2 | Las Yungas (Oran, Salta) | V 5 | 205 lts/ha |

TABLE B

Results

| | amount of ai Novaluron, g/ha | amount of ai Spinetoram, g/ha | % Efficacy of control | | |
|---|---|---|---|---|---|
| | | | 1 DAA | 3 DAA | 7 DAA |
| Trial 1 | | | | | |
| % of Efficacy (according to number of larva/plant) | | | | | |
| 1 Novaluron + Spinetoram | 7.5 | 7.5 | 97.78% | 100.00% | 100.00% |
| 2 Novaluron + Spinetoram | 7.5 | 5.625 | 95.56% | 100.00% | 100.00% |

TABLE B-continued

| | | amount of ai | amount of ai | % Efficacy of control | | |
|---|---|---|---|---|---|---|
| | | Novaluron, g/ha | Spinetoram, g/ha | 1 DAA | 3 DAA | 7 DAA |
| 3 | Novaluron + Spinetoram | 7.5 | 3.75 | 95.56% | 100.00% | 100.00% |
| 4 | Novaluron + Spinetoram | 7.5 | 1.875 | 82.22% | 96.97% | 100.00% |
| 5 | Novaluron + Spinetoram | 5.625 | 7.5 | 100.00% | 98.48% | 100.00% |
| 6 | Novaluron + Spinetoram | 5.625 | 5.625 | 100.00% | 96.97% | 97.01% |
| 7 | Novaluron + Spinetoram | 5.625 | 3.75 | 88.89% | 96.97% | 98.51% |
| 8 | Novaluron + Spinetoram | 5.625 | 1.875 | 93.33% | 95.45% | 92.54% |
| 9 | Novaluron + Spinetoram | 3.75 | 7.5 | 84.44% | 93.94% | 91.04% |
| 10 | Novaluron + Spinetoram | 3.75 | 5.625 | 68.89% | 90.91% | 86.57% |
| 11 | Novaluron + Spinetoram | 3.75 | 3.75 | 64.44% | 90.91% | 83.58% |
| 12 | Novaluron + Spinetoram | 3.75 | 1.875 | 57.78% | 80.30% | 85.07% |
| 13 | Novaluron + Spinetoram | 1.875 | 7.5 | 55.56% | 80.30% | 80.60% |
| 14 | Novaluron + Spinetoram | 1.875 | 5.625 | 51.11% | 77.27% | 68.66% |
| 15 | Novaluron + Spinetoram | 1.875 | 3.75 | 42.22% | 65.15% | 64.18% |
| 16 | Novaluron + Spinetoram | 1.875 | 1.875 | 31.11% | 74.24% | 52.24% |
| 17 | Novaluron | 7.5 | 0 | 77.78% | 93.94% | 83.58% |
| 18 | Spinetoram | 0 | 7.5 | 77.78% | 96.97% | 89.55% |
| 19 | Novaluron | 5.625 | 0 | 66.67% | 89.39% | 76.12% |
| 20 | Spinetoram | 0 | 5.625 | 71.11% | 84.85% | 76.12% |
| 21 | Novaluron | 3.75 | 0 | 51.11% | 78.79% | 65.67% |
| 22 | Spinetoram | 0 | 3.75 | 64.44% | 78.79% | 59.70% |
| 23 | Novaluron | 1.875 | 0 | 35.56% | 63.64% | 46.27% |
| 24 | Spinetoram | 0 | 1.875 | 44.44% | 62.12% | 50.75% |
| 25 | Untreated controls (UTC) | 0 | 0 | 0.00% | 0.00% | 0.00% |
| Trial 2 | | | | | | |
| % of Efficacy (according to number of larva/plant) | | | | | | |
| 1 | Novaluron + Spinetoram | 7.5 | 7.5 | 68.42% | 92.45% | 100.00% |
| 2 | Novaluron + Spinetoram | 7.5 | 5.625 | 68.42% | 84.91% | 100.00% |
| 3 | Novaluron + Spinetoram | 7.5 | 3.75 | 62.28% | 94.34% | 98.28% |
| 4 | Novaluron + Spinetoram | 7.5 | 1.875 | 60.53% | 86.79% | 93.10% |
| 5 | Novaluron + Spinetoram | 5.625 | 7.5 | 63.16% | 92.45% | 100.00% |
| 6 | Novaluron + Spinetoram | 5.625 | 5.625 | 63.16% | 94.34% | 98.28% |
| 7 | Novaluron + Spinetoram | 5.625 | 3.75 | 50.00% | 84.91% | 98.28% |
| 8 | Novaluron + Spinetoram | 5.625 | 1.875 | 55.26% | 81.13% | 87.93% |
| 9 | Novaluron + Spinetoram | 3.75 | 7.5 | 65.79% | 83.02% | 94.83% |
| 10 | Novaluron + Spinetoram | 3.75 | 5.625 | 50.00% | 81.13% | 89.66% |
| 11 | Novaluron + Spinetoram | 3.75 | 3.75 | 47.37% | 84.91% | 84.48% |
| 12 | Novaluron + Spinetoram | 3.75 | 1.875 | 42.11% | 71.70% | 70.69% |
| 13 | Novaluron + Spinetoram | 1.875 | 7.5 | 44.74% | 73.58% | 75.86% |
| 14 | Novaluron + Spinetoram | 1.875 | 5.625 | 47.37% | 69.81% | 75.86% |
| 15 | Novaluron + Spinetoram | 1.875 | 3.75 | 34.21% | 62.26% | 56.90% |
| 16 | Novaluron + Spinetoram | 1.875 | 1.875 | 31.58% | 49.06% | 53.45% |
| 17 | Novaluron | 7.5 | 0 | 55.26% | 71.70% | 82.76% |
| 18 | Spinetoram | 0 | 7.5 | 44.74% | 71.70% | 84.48% |
| 19 | Novaluron | 5.625 | 0 | 42.11% | 64.15% | 70.69% |
| 20 | Spinetoram | 0 | 5.625 | 55.26% | 71.70% | 82.76% |
| 21 | Novaluron | 3.75 | 0 | 26.32% | 58.49% | 62.07% |
| 22 | Spinetoram | 0 | 3.75 | 31.58% | 64.15% | 72.41% |
| 23 | Novaluron | 1.875 | 0 | 28.95% | 49.06% | 60.34% |
| 24 | Spinetoram | 0 | 1.875 | 15.79% | 45.28% | 65.52% |
| 25 | Untreated controls (UTC) | 0 | 0 | 0.00% | 0.00% | 0.00% |

Example 3

Foliar applications of Pyriproxyfen and Spinetoram on Whitefly (*Trialeurodes vaporariorum*) Control in Peppers (*Capsicum annuum*)

The efficacy of Pyriproxyfen and Spinetoram on whitefly control in pepper crops was evaluated.

Two trials were conducted on pepper crops in the vegetable growing belt of La Plata (Province of Buenos Aires, Argentina) with the goal of evaluating the efficacy and interaction of foliar applications of Pyriproxyfen and Spinetoram on whiteflies. For preparation of the mixtures, Spinetoram product used is the same as in Example 1, Pyriproxyfen (EPINGLE® 1.00 g a.i./L. EC, Sumitomo Chemical Co., Ltd.) was used. Applications were made using a backpack-type sprayer fitted with a vertical bar and a constant pressure regulator, with nozzles set at 0.30 m from one another and fitted with 8002 flat fan tips. In all cases, applications were made at a rate of 900-915 l·ha (L/ha). Eight-meter-long plots were used, each divided into four ridges (eight rows of plants). Applications were made on two ridges, while the remaining two ridges were left as buffers. Experiment design consisted in random blocks at four repetitions.

The number of adult whiteflies per leaf was assessed e.g. at days 1, 3, 5, 7, 10 and 14 post-application, whereas the number of whitefly nymphs per leaf was evaluated e.g. at 10, 14, 21 and 29 days post-application. For this assessment, ten leaves were taken from plants located in the central rows of each plot, taking care to avoid the initial and final meter of each plot. Efficacy of control (%) was calculated based on untreated control.

Description of Each Trial

| Location | Phenological Status | Rate of application ($l \cdot ha^{-1}$) |
|---|---|---|
| Trial 1 Jurado (Olmos) | Harvest | 900 lts/ha |
| Trial 2 Expovictor (Florencio Varela) | Harvest | 915 lts/ha |

Results

Trial 1

| | amount of ai Spinetoram, g/ha | amount of ai Pyriproxyfen, g/ha | Efficacy of control (%) | | | | | | | | | |
|---|---|---|---|---|---|---|---|---|---|---|---|---|
| | | | Adults | | | | | | Nymphs | | | |
| | | | 1 DAA | 3 DAA | 5 DAA | 7 DAA | 10 DAA | 14 DAA | 10 DAA | 14 DAA | 21 DAA | 29 DAA |
| 1 | 60.0 | 100 | 66.57% | 78.44% | 70.26% | 77.57% | 68.79% | 81.74% | 100.00% | 94.82% | 100.00% | 96.08% |
| 2 | 60.0 | 75 | 67.57% | 78.89% | 77.59% | 71.21% | 72.67% | 78.34% | 100.00% | 93.06% | 100.00% | 96.85% |
| 3 | 60.0 | 50 | 53.20% | 66.32% | 61.25% | 45.42% | 55.13% | 66.88% | 100.00% | 65.53% | 86.16% | 96.06% |
| 4 | 60.0 | 25 | 46.51% | 54.34% | 52.24% | 29.72% | 45.56% | 57.75% | 93.42% | 82.82% | 96.49% | 98.43% |
| 5 | 45.0 | 100 | 61.31% | 70.06% | 73.82% | 76.64% | 60.36% | 75.37% | 93.42% | 94.82% | 100.00% | 98.43% |
| 6 | 45.0 | 75 | 57.33% | 67.37% | 65.86% | 57.38% | 56.72% | 59.02% | 87.23% | 70.70% | 51.86% | 98.43% |
| 7 | 45.0 | 50 | 48.08% | 57.93% | 56.01% | 49.72% | 52.62% | 50.96% | 70.99% | 62.01% | 72.52% | 95.28% |
| 8 | 45.0 | 25 | 43.24% | 52.69% | 47.21% | 34.21% | 35.76% | 39.28% | 74.27% | 36.23% | 89.67% | 90.55% |
| 9 | 30.0 | 100 | 53.20% | 67.66% | 66.28% | 77.57% | 61.05% | 67.52% | 74.08% | 82.71% | 96.49% | 98.43% |
| 10 | 30.0 | 75 | 48.65% | 64.52% | 61.25% | 70.84% | 46.01% | 58.17% | 90.33% | 58.59% | 89.67% | 59.06% |
| 11 | 30.0 | 50 | 40.97% | 48.35% | 43.65% | 48.04% | 33.49% | 56.05% | 80.66% | 62.11% | 62.19% | 96.06% |
| 12 | 30.0 | 25 | 29.59% | 42.81% | 41.14% | 31.96% | 26.42% | 42.04% | 83.75% | 43.06% | 72.52% | 88.98% |
| 13 | 15.0 | 100 | 53.49% | 64.67% | 63.55% | 82.43% | 56.95% | 71.97% | 83.75% | 67.29% | 86.36% | 85.04% |
| 14 | 15.0 | 75 | 40.54% | 42.07% | 51.40% | 58.69% | 41.69% | 47.98% | 77.37% | 48.34% | −10.33% | 59.85% |
| 15 | 15.0 | 50 | 36.98% | 41.92% | 34.44% | 45.61% | 31.44% | 39.28% | 83.95% | 62.01% | 89.67% | 85.04% |
| 16 | 15.0 | 25 | 33.85% | 39.97% | 33.39% | 23.36% | 21.64% | 31.85% | 83.75% | 63.77% | 82.85% | 93.70% |
| 17 | 60.0 | 0 | 32.15% | 44.76% | 54.96% | 55.14% | 35.54% | 42.68% | 54.74% | 51.66% | 37.40% | 74.79% |
| 18 | 0.0 | 100 | 43.53% | 63.02% | 63.55% | 69.35% | 56.95% | 45.65% | 67.89% | 51.76% | 69.01% | 88.19% |
| 19 | 15.0 | 0 | 10.10% | 15.27% | 0.71% | 9.16% | −16.17% | −14.65% | 61.32% | 8.59% | −3.31% | 61.41% |
| 20 | 0.0 | 25 | 19.20% | 30.09% | 25.01% | 36.64% | 18.91% | 9.55% | 54.74% | 24.12% | 58.68% | 73.25% |
| 21 | 45.0 | 0 | 20.34% | 29.19% | 32.76% | 31.96% | 23.46% | 12.95% | 45.26% | 41.30% | 30.99% | 74.00% |
| 22 | 0.0 | 75 | 19.91% | 55.84% | 47.84% | 64.49% | 45.56% | 35.46% | 48.55% | 46.48% | 62.19% | 87.40% |
| 23 | 30.0 | 0 | 34.00% | 38.62% | 8.67% | 37.57% | 21.64% | 5.94% | 74.08% | 17.18% | 10.74% | 78.73% |
| 24 | 0.0 | 50 | 34.00% | 55.69% | 39.04% | 57.01% | 33.71% | 29.51% | 80.85% | 51.66% | 38.02% | 90.57% |
| 25 | 0.0 | 0 | 0% | 0% | 0% | 0% | 0% | 0% | 0% | 0% | 0% | 0% |

| | | | Trial 2 | | | | | | |
|---|---|---|---|---|---|---|---|---|---|
| | | | | | Efficacy of control (%) | | | | |
| | a.i. | a.i. | | Adults | | | | Nymphs | |
| | Spin[a] g/ha | Pyr[b] g/ha | 1 DAA | 3 DAA | 6 DAA | 8 DAA | 11 DAA | 17 DAA | 22 DAA | 30 DAA |
|---|---|---|---|---|---|---|---|---|---|---|
| 1 | 60.0 | 100 | 67.01% | 80.58% | 64.82% | 74.78% | 97.02% | 97.28% | 83.39% | 97.51% |
| 2 | 60.0 | 75 | 52.82% | 69.70% | 58.33% | 61.64% | 85.09% | 81.85% | 68.94% | 82.61% |
| 3 | 60.0 | 50 | 50.00% | 66.03% | 50.89% | 53.22% | 41.74% | 61.14% | 35.24% | 73.50% |
| 4 | 60.0 | 25 | 32.76% | 54.87% | 39.52% | 38.83% | 68.58% | 71.20% | 29.87% | 61.47% |
| 5 | 45.0 | 100 | 66.72% | 66.10% | 67.44% | 61.42% | 86.24% | 82.26% | 66.07% | 82.73% |
| 6 | 45.0 | 75 | 57.13% | 62.36% | 53.75% | 58.51% | 78.67% | 58.50% | 61.41% | 78.80% |
| 7 | 45.0 | 50 | 54.61% | 54.45% | 52.20% | 40.66% | 64.22% | 64.19% | 55.91% | 72.88% |
| 8 | 45.0 | 25 | 42.42% | 40.54% | 39.58% | 36.45% | 66.28% | 66.42% | −0.48% | 68.77% |
| 9 | 30.0 | 100 | 66.86% | 65.96% | 66.13% | 68.84% | 80.28% | 72.36% | 63.68% | 70.64% |
| 10 | 30.0 | 75 | 64.49% | 62.99% | 57.26% | 60.67% | 84.17% | 70.96% | 58.78% | 72.26% |
| 11 | 30.0 | 50 | 50.00% | 48.02% | 44.46% | 52.18% | 57.11% | 58.83% | 30.47% | 49.00% |
| 12 | 30.0 | 25 | 38.48% | 40.32% | 42.32% | 42.25% | 63.53% | 43.32% | 18.04% | 63.97% |
| 13 | 15.0 | 100 | 63.74% | 65.18% | 65.24% | 66.39% | 78.90% | 64.52% | 62.84% | 72.94% |
| 14 | 15.0 | 75 | 53.49% | 51.98% | 49.76% | 50.27% | 69.50% | 60.15% | 57.59% | 51.00% |
| 15 | 15.0 | 50 | 48.29% | 58.19% | 45.54% | 42.25% | 57.11% | 39.69% | 46.36% | 58.85% |
| 16 | 15.0 | 25 | 37.59% | 41.03% | 33.15% | 29.11% | 56.65% | 48.35% | 14.81% | 27.56% |
| 17 | 60.0 | 0 | 52.60% | 53.18% | 42.02% | 55.42% | 64.22% | 61.72% | 36.80% | 56.92% |
| 18 | 0.0 | 100 | 67.01% | 64.97% | 64.58% | 59.70% | 85.32% | 70.21% | 57.23% | 76.43% |
| 19 | 15.0 | 0 | 13.97% | 7.63% | 10.18% | 13.35% | 12.16% | 27.81% | −17.32% | 18.89% |
| 20 | 0.0 | 25 | 28.90% | 10.24% | 15.24% | 30.51% | 60.09% | 37.21% | 14.93% | 33.29% |
| 21 | 45.0 | 0 | 37.74% | 35.24% | 24.40% | 45.56% | 50.00% | 39.36% | 19.95% | 36.10% |
| 22 | 0.0 | 75 | 46.14% | 48.23% | 33.93% | 44.04% | 69.27% | 47.44% | 58.30% | 58.98% |
| 23 | 30.0 | 0 | 33.51% | 19.77% | 9.05% | 32.24% | 44.72% | 9.90% | −0.72% | 45.01% |
| 24 | 0.0 | 50 | 43.39% | 31.00% | 33.27% | 41.17% | 61.70% | 48.84% | 30.11% | 41.90% |
| 25 | 0.0 | 0 | 0% | 0% | 0% | 0% | 0% | 0% | 0% | 0% |

[a]Spinetoram;
[b]Pyriproxyfen

Example 4

Foliar Applications of Pyriproxyfen and Spinetoram on Western Flower Thrips (*Frankliniella occidentalis*) in Peppers (*Capsicum annuum*)

The study was conducted to assess the efficacy of and interaction between Pyriproxyfen and Spinetoram on Western flower *thrips* in pepper crops.

Two trials were conducted on pepper crops in the vegetable growing belt of La Plata (Province of Buenos Aires, Argentina) with the goal of evaluating the efficacy and interaction of foliar applications of Pyriproxyfen and Spinetoram on Western flower *thrips*. For preparation of the mixtures, the products used are the same as in Example 3.

Applications were made using a backpack-type sprayer fitted with a vertical bar and a constant pressure regulator, with nozzles set at 0.30 m from one another and fitted with 8002 flat fan tips. In all cases, applications were made at a rate of 790-937 l·ha$^{-1}$. Eight-meter-long plots were used, each divided into four ridges (eight rows of plants). Applications were made on two ridges, while the remaining two ridges were left as buffers. Experiment design consisted in random blocks at four repetitions.

The number of *thrips* (all stages) per flower was assessed at days e.g. 1, 3, 5, 7, 10 and 14 post-application. For this assessment, ten flowers were taken from plants located in the central rows of each plot, taking care to avoid the initial and final meter of each plot. Efficacy of control (%) was calculated based on untreated control.

Detailed Description of Each Trial:

| Location | Phenological Status | Rate of application (l · ha$^{-1}$) |
|---|---|---|
| Trial 1  Jurado (Olmos) | Harvest | 937 lts/ha |
| Trial 2  Expovictor (Florencio Varela) | Harvest | 790 lts/ha |

| | | Trial 1 | | | | | | |
|---|---|---|---|---|---|---|---|---|
| | amount of ai | amount of ai | | | Efficacy of control (%) | | | |
| | Spinetoram, g/ha | Pyriproxyfen, g/ha | 1 DAA | 3 DAA | 5 DAA | 7 DAA | 10 DAA | 14 DAA |
| 1 | 60.0 | 100 | 81.38% | 92.21% | 95.94% | 89.42% | 88.59% | 77.33% |
| 2 | 60.0 | 75 | 67.02% | 80.33% | 83.25% | 80.77% | 78.52% | 72.44% |
| 3 | 60.0 | 50 | 62.23% | 71.72% | 82.74% | 75.96% | 79.19% | 61.33% |
| 4 | 60.0 | 25 | 48.94% | 65.16% | 76.65% | 68.27% | 65.77% | 53.33% |
| 5 | 45.0 | 100 | 69.15% | 71.31% | 90.36% | 81.73% | 83.89% | 63.11% |
| 6 | 45.0 | 75 | 43.62% | 69.26% | 85.28% | 73.08% | 72.48% | 49.33% |
| 7 | 45.0 | 50 | 36.17% | 59.02% | 78.68% | 72.12% | 70.47% | 42.53% |
| 8 | 45.0 | 25 | 39.89% | 59.02% | 76.14% | 64.42% | 59.06% | 21.78% |

-continued

| Trial 1 | | | | | | | | |
|---|---|---|---|---|---|---|---|---|
| | amount of ai | amount of ai | Efficacy of control (%) | | | | | |
| | Spinetoram, g/ha | Pyriproxyfen, g/ha | 1 DAA | 3 DAA | 5 DAA | 7 DAA | 10 DAA | 14 DAA |
| 9 | 30.0 | 100 | 73.40% | 71.31% | 87.31% | 64.42% | 72.48% | 49.24% |
| 10 | 30.0 | 75 | 50.53% | 59.02% | 71.07% | 56.73% | 53.69% | 36.44% |
| 11 | 30.0 | 50 | 38.30% | 48.36% | 72.59% | 51.92% | 55.03% | 41.33% |
| 12 | 30.0 | 25 | 35.64% | 39.75% | 60.91% | 37.50% | 42.95% | 24.44% |
| 13 | 15.0 | 100 | 52.13% | 70.12% | 80.71% | 59.62% | 69.13% | 47.56% |
| 14 | 15.0 | 75 | 45.21% | 47.54% | 80.20% | 48.08% | 54.36% | 38.22% |
| 15 | 15.0 | 50 | 23.94% | 40.98% | 71.57% | 40.38% | 50.34% | 36.89% |
| 16 | 15.0 | 25 | 21.81% | 41.39% | 62.44% | 32.69% | 48.32% | 28.44% |
| 17 | 60.0 | 0 | 43.62% | 70.90% | 83.25% | 61.54% | 65.10% | 47.56% |
| 18 | 0.0 | 100 | 22.34% | 64.34% | 81.73% | 57.69% | 65.77% | 36.44% |
| 19 | 15.0 | 0 | 6.38% | 30.33% | 41.12% | 1.92% | 23.49% | 23.11% |
| 20 | 0.0 | 25 | 12.77% | 28.69% | 61.42% | 33.65% | 34.23% | 29.33% |
| 21 | 45.0 | 0 | 30.85% | 45.49% | 59.39% | 53.85% | 63.76% | 22.22% |
| 22 | 0.0 | 75 | 27.66% | 49.18% | 63.45% | 50.00% | 65.77% | 42.67% |
| 23 | 30.0 | 0 | 17.55% | 41.80% | 42.13% | 18.27% | 32.21% | 25.78% |
| 24 | 0.0 | 50 | 40.43% | 43.03% | 48.73% | 47.12% | 40.27% | 45.78% |
| 25 | 0.0 | 0 | 0% | 0% | 0% | 0% | 0% | 0% |

| Trial 2 | | | | | | | |
|---|---|---|---|---|---|---|---|
| | | mount of ai | amount of ai | Efficacy of control (%) | | | |
| | | Spinetoram g/ha | Pyriproxyfen g/ha | 1 DAA | 3 DAA | 6 DAA | 8 DAA |
| 1 | Pyriproxyfen + Spinetoram | 60.0 | 100 | 73.11% | 91.49% | 75.10% | 72.53% |
| 2 | Pyriproxyfen + Spinetoram | 60.0 | 75 | 61.86% | 85.49% | 69.22% | 67.79% |
| 3 | Pyriproxyfen + Spinetoram | 60.0 | 50 | 58.68% | 76.40% | 57.16% | 52.77% |
| 4 | Pyriproxyfen + Spinetoram | 60.0 | 25 | 50.12% | 67.12% | 54.90% | 55.73% |
| 5 | Pyriproxyfen + Spinetoram | 45.0 | 100 | 78.48% | 78.53% | 68.14% | 63.44% |
| 6 | Pyriproxyfen + Spinetoram | 45.0 | 75 | 57.70% | 70.60% | 61.76% | 54.35% |
| 7 | Pyriproxyfen + Spinetoram | 45.0 | 50 | 60.15% | 62.67% | 52.35% | 53.56% |
| 8 | Pyriproxyfen + Spinetoram | 45.0 | 25 | 53.30% | 60.74% | 54.61% | 52.96% |
| 9 | Pyriproxyfen + Spinetoram | 30.0 | 100 | 64.06% | 73.69% | 65.69% | 70.16% |
| 10 | Pyriproxyfen + Spinetoram | 30.0 | 75 | 61.12% | 61.70% | 63.24% | 56.72% |
| 11 | Pyriproxyfen + Spinetoram | 30.0 | 50 | 45.97% | 55.71% | 51.67% | 50.20% |
| 12 | Pyriproxyfen + Spinetoram | 30.0 | 25 | 46.45% | 50.48% | 50.10% | 55.73% |
| 13 | Pyriproxyfen + Spinetoram | 15.0 | 100 | 66.75% | 64.60% | 64.61% | 64.23% |
| 14 | Pyriproxyfen + Spinetoram | 15.0 | 75 | 64.30% | 62.67% | 48.63% | 52.96% |
| 15 | Pyriproxyfen + Spinetoram | 15.0 | 50 | 55.01% | 47.97% | 47.45% | 53.95% |
| 16 | Pyriproxyfen + Spinetoram | 15.0 | 25 | 37.65% | 52.22% | 42.35% | 44.66% |
| 17 | Spinetoram | 60.0 | 0 | 55.99% | 61.70% | 70.88% | 62.06% |
| 18 | Pyriproxyfen | 0.0 | 100 | 31.30% | 47.20% | 43.14% | 44.86% |
| 19 | Spinetoram | 15.0 | 0 | 30.56% | 28.63% | 33.04% | 16.01% |
| 20 | Pyriproxyfen | 0.0 | 25 | 16.14% | 17.79% | 19.22% | −14.82% |
| 21 | Spinetoram | 45.0 | 0 | 38.14% | 43.91% | 55.10% | 50.40% |
| 22 | Pyriproxyfen | 0.0 | 75 | 35.45% | 32.11% | 16.08% | 32.61% |
| 23 | Spinetoram | 30.0 | 0 | 37.90% | 39.85% | 39.12% | 33.20% |
| 24 | Pyriproxyfen | 0.0 | 50 | 35.70% | 22.05% | 28.92% | 37.55% |
| 25 | Untreated controls (UTC) | 0 | 0 | 0% | 0% | 0% | 0% |

Example 5

Foliar Applications of Tau-Fluvalinate and Spinetoram on Whiteflies (*Trialeurodes vaporariorum*) in Peppers (*Capsicum annuum*)

Two trials were conducted on pepper crops in the vegetable growing belt of La Plata (Province of Buenos Aires, Argentina) with the goal of evaluating the efficacy and interaction of foliar applications of Tau-fluvalinate and Spinetoram in whitefly control. For preparation of the mixtures, Spinetoram product used was the same as in Example 1, Tau-fluvalinate (Mavrik® 240 g a.i./L EW, Makhteshim Agan Group Company) was used.

Applications were made using a backpack-type sprayer fitted with a vertical bar and a constant pressure regulator, with nozzles set at 0.30 in from one another and fitted with 8002 flat fan tips. In all cases, applications were made at a rate of 810-900 l·ha$^{-1}$. Eight-meter-long plots were used, each divided into four ridges (eight rows of plants). Applications were made on two ridges, while the remaining two ridges were left as buffers. Experiment design consisted in random blocks at four repetitions.

The number of adult whiteflies per leaf was assessed at days e.g. 1, 3, 5, 7, 10 and 14 post-application, whereas the number of whitefly nymphs per leaf was evaluated at e.g. 11, 15 and 21 days post-application. For this assessment, ten leaves were taken from plants located in the central rows of each plot, taking care to avoid the initial and final meter of each plot. Efficacy of Control (%) was calculated based on untreated control.

TABLE A

Detailed description of each trial

| | Location | Phenological Status | Rate of application (l/ha) |
|---|---|---|---|
| Trial 1 | Serrano (Olmos) | Harvest | 900 lts/ha |
| Trial 2 | Expovictor (Florencio Varela) | Harvest | 810 lts/ha |

Results

| | | | Trial 1 | | | | | | | | |
|---|---|---|---|---|---|---|---|---|---|---|---|
| | | | Efficacy of control (%) | | | | | | | | |
| | amount of ai | amount of ai | Adults | | | | | | Nymphs | | |
| | Spinetoram g/ha | Tau-fluvalinate g/ha | 1 DAA | 3 DAA | 5 DAA | 7 DAA | 10 DAA | 14 DAA | 11 DAA | 15 DAA | 21 DAA |
| 1 | 60.0 | 30 | 69.60% | 83.64% | 76.85% | 80.28% | 81.09% | 65.31% | 94.44% | 95.28% | 71.88% |
| 2 | 60.0 | 22.5 | 61.85% | 71.78% | 70.85% | 68.71% | 69.83% | 64.25% | 76.03% | 85.32% | 56.05% |
| 3 | 60.0 | 15 | 32.50% | 57.10% | 51.81% | 60.14% | 62.73% | 60.07% | 68.71% | 79.87% | 64.04% |
| 4 | 60.0 | 7.5 | -4.78% | 41.40% | 41.21% | 57.89% | 61.34% | 60.47% | 61.41% | 78.44% | 44.62% |
| 5 | 45.0 | 30 | 66.06% | 82.20% | 70.08% | 72.56% | 74.90% | 72.75% | 78.36% | 86.45% | 84.08% |
| 6 | 45.0 | 22.5 | 48.09% | 70.52% | 44.00% | 64.92% | 68.78% | 64.54% | 75.44% | 55.03% | 33.07% |
| 7 | 45.0 | 15 | 7.07% | 57.28% | 25.52% | 49.32% | 56.23% | 51.44% | 65.20% | 70.02% | 43.19% |
| 8 | 45.0 | 7.5 | -19.60% | 44.16% | 13.39% | 20.66% | 27.84% | 36.15% | 51.75% | 66.53% | 26.12% |
| 9 | 30.0 | 30 | 61.85% | 74.00% | 63.46% | 70.63% | 74.84% | 69.17% | 64.04% | 87.16% | 68.72% |
| 10 | 30.0 | 22.5 | 37.76% | 59.20% | 46.51% | 59.72% | 67.25% | 66.21% | 64.62% | 58.62% | 55.25% |
| 11 | 30.0 | 15 | 18.07% | 32.53% | 25.66% | 46.42% | 57.12% | 58.44% | 54.39% | 68.58% | 47.09% |
| 12 | 30.0 | 7.5 | -1.53% | 20.49% | -3.84% | 28.34% | 41.94% | 42.86% | 30.12% | 56.98% | 31.14% |
| 13 | 15.0 | 30 | 65.11% | 73.64% | 59.83% | 68.06% | 74.09% | 67.14% | 61.12% | 81.83% | 79.26% |
| 14 | 15.0 | 22.5 | 41.30% | 55.78% | 39.26% | 56.25% | 65.56% | 61.41% | 45.91% | 69.94% | 42.17% |
| 15 | 15.0 | 15 | 4.88% | 33.25% | 20.01% | 37.66% | 49.83% | 53.44% | 51.75% | 54.43% | 41.59% |
| 16 | 15.0 | 7.5 | -31.17% | 14.44% | -3.07% | 16.02% | 30.87% | 38.43% | 42.11% | 39.02% | 18.84% |
| 17 | 60.0 | 0 | 32.31% | 45.66% | 34.59% | 44.96% | 45.66% | 53.07% | 59.36% | 83.57% | 56.61% |
| 18 | 0.0 | 30 | 44.84% | 64.29% | 53.84% | 57.00% | 62.38% | 68.81% | 68.42% | 74.84% | 67.17% |
| 19 | 15.0 | 0 | 4.11% | 16.00% | 5.23% | 29.51% | 25.81% | 45.30% | 40.94% | 55.44% | 40.58% |
| 20 | 0.0 | 7.5 | 14.05% | 39.78% | 23.92% | 46.84% | 52.61% | 49.98% | 40.64% | 62.01% | 40.92% |
| 21 | 45.0 | 0 | 14.63% | 37.09% | 20.15% | 40.89% | 43.33% | 49.90% | 41.82% | 67.76% | 48.99% |
| 22 | 0.0 | 22.5 | 21.32% | 49.07% | 30.61% | 51.52% | 62.53% | 58.85% | 38.30% | 69.40% | 62.67% |
| 23 | 30.0 | 0 | -3.25% | 21.51% | 0.56% | 22.62% | 31.91% | 41.76% | 21.92% | 54.41% | 41.03% |
| 24 | 0.0 | 15 | 14.53% | 40.86% | 20.78% | 39.63% | 52.90% | 49.00% | 47.66% | 64.27% | 46.97% |

Trial 2

| | amount of ai Spinetoram g/ha | amount of ai Tau-fluvalinate g/ha | Efficacy of control (%) | | | | | | |
|---|---|---|---|---|---|---|---|---|---|
| | | | Adults | | | | Nymphs | | |
| | | | 1 DAA | 3 DAA | 6 DAA | 10 DAA | 14 DAA | 21 DAA | 28 DAA |
| 1 | 60.0 | 72.0 | 4.38% | 72.91% | 90.30% | 78.32% | 76.47% | 84.45% | 75.95% |
| 2 | 60.0 | 54.0 | 2.92% | 58.88% | 82.49% | 61.70% | 46.04% | 79.08% | 62.78% |
| 3 | 60.0 | 36.0 | −5.22% | 41.51% | 73.74% | 51.67% | 41.43% | 73.02% | 58.69% |
| 4 | 60.0 | 18.0 | 7.72% | 29.05% | 55.35% | 38.96% | 50.12% | 58.36% | 37.58% |
| 5 | 45.0 | 72.0 | 4.80% | 74.39% | 76.57% | 69.76% | 70.85% | 83.85% | 65.74% |
| 6 | 45.0 | 54.0 | −0.42% | 64.47% | 72.19% | 60.07% | 59.60% | 71.30% | 44.21% |
| 7 | 45.0 | 36.0 | 4.18% | 35.82% | 56.03% | 34.96% | 58.57% | 62.08% | 31.68% |
| 8 | 45.0 | 18.0 | 4.80% | 26.99% | 54.81% | 36.46% | 71.86% | 37.14% | 6.31% |
| 9 | 30.0 | 72.0 | 10.86% | 77.13% | 80.40% | 70.01% | 74.70% | 73.15% | 55.50% |
| 10 | 30.0 | 54.0 | 1.25% | 55.35% | 66.33% | 56.89% | 71.61% | 60.92% | 48.25% |
| 11 | 30.0 | 36.0 | −3.13% | 50.44% | 62.56% | 50.77% | 58.30% | 43.71% | 26.24% |
| 12 | 30.0 | 18.0 | 5.64% | 49.95% | 67.14% | 53.14% | 66.23% | 40.41% | 16.48% |
| 13 | 15.0 | 72.0 | 1.46% | 81.26% | 81.82% | 74.98% | 58.82% | 62.72% | 49.16% |
| 14 | 15.0 | 54.0 | 9.81% | 63.40% | 76.23% | 59.58% | 57.54% | 59.32% | 34.62% |
| 15 | 15.0 | 36.0 | 12.11% | 49.66% | 62.22% | 46.70% | 54.48% | 37.65% | 10.62% |
| 16 | 15.0 | 18.0 | −1.67% | 46.91% | 55.29% | 44.01% | 50.13% | 39.78% | 7.89% |
| 17 | 60.0 | 0.0 | 7.31% | 39.74% | 54.07% | 41.73% | 51.92% | 46.70% | 27.36% |
| 18 | 0.0 | 72.0 | 11.06% | 58.88% | 71.45% | 59.74% | 71.10% | 73.66% | 59.37% |
| 19 | 15.0 | 0.0 | −6.26% | −19.92% | 18.92% | −1.87% | 37.60% | 22.78% | −21.39% |
| 20 | 0.0 | 18.0 | 3.55% | 18.25% | 34.61% | 7.74% | 54.73% | 37.55% | −17.56% |
| 21 | 45.0 | 0.0 | −15.45% | 31.01% | 52.19% | 29.83% | 57.03% | 41.27% | 6.48% |
| 22 | 0.0 | 54.0 | −15.03% | 56.82% | 64.44% | 43.60% | 62.67% | 58.68% | 11.29% |
| 23 | 30.0 | 0.0 | −14.20% | 12.07% | 25.32% | 18.91% | 49.37% | 32.44% | −15.76% |
| 24 | 0.0 | 36.0 | 1.67% | 22.96% | 48.35% | 10.27% | 67.97% | 50.50% | 1.95% |
| 25 | 0.0 | 0 | 0% | 0% | 0% | 0% | 0% | 0% | 0% |

Example 6

Foliar Applications of Tau-Fluvalinate and Spinetoram on Western Flower *Thrips* (*Frankliniella occidentalis*) in Peppers (*Capsicum annuum*)

The study was conducted to assess the efficacy of and interaction between Tau-fluvalinate and Spinetoram on Western flower *thrips* in pepper crops.

Two trials were conducted on pepper crops in the vegetable growing belt of La Plata (Province of Buenos Aires, Argentina) with the goal of evaluating the efficacy and interaction of foliar applications of Tau-fluvalinate and Spinetoram on Western flower *thrips*.

Applications were made using a backpack-type sprayer fitted with a vertical bar and a constant pressure regulator, with nozzles set at 0.30 m from one another and fitted with 8002 flat fan tips. In all cases, applications were made at a rate of 790-937 l·ha$^{-1}$. Eight-meter-long plots were used, each divided into four ridges (eight rows of plants). Applications were made on two ridges, while the remaining two ridges were left as buffers. Experiment design consisted in random blocks at four repetitions.

The number of *thrips* (all stages) per flower was assessed at days e.g. 1, 3, 5, 7, 10 and 14 post-application. For this assessment, ten flowers were taken from plants located in the central rows of each plot, taking care to avoid the initial and final meter of each plot. Efficacy of Control (%) was calculated based on untreated control.

Description of Each Trial

| Location | | Phenological Status | Rate of application (l · ha) |
|---|---|---|---|
| Trial 1 | Serrano (Olmos) | Harvest | 937 lts/ha |
| Trial 2 | Expovictor (Florencio Varela) | Harvest | 790 lts/ha |

Trial 1

| | amount of ai Spinetoram, g/ha | amount of ai Tau-fluvalinate, g/ha | Efficacy of control (%) | | | | | |
|---|---|---|---|---|---|---|---|---|
| | | | 1 DAA | 3 DAA | 5 DAA | 7 DAA | 10 DAA | 14 DAA |
| 1 | 60.0 | 72.0 | 44.33% | 86.49% | 97.67% | 93.91% | 90.51% | 81.96% |
| 2 | 60.0 | 54.0 | 39.63% | 82.14% | 87.67% | 87.54% | 80.09% | 76.26% |
| 3 | 60.0 | 36.0 | 27.57% | 75.16% | 80.00% | 79.42% | 78.47% | 63.24% |
| 4 | 60.0 | 18.0 | 35.61% | 64.05% | 70.47% | 67.83% | 73.15% | 53.42% |
| 5 | 45.0 | 72.0 | 23.88% | 77.78% | 86.74% | 76.81% | 83.80% | 77.40% |
| 6 | 45.0 | 54.0 | 39.30% | 69.50% | 73.72% | 74.78% | 74.07% | 68.49% |
| 7 | 45.0 | 36.0 | 20.52% | 59.91% | 60.93% | 64.35% | 69.21% | 56.85% |
| 8 | 45.0 | 18.0 | 27.57% | 54.90% | 55.12% | 51.30% | 65.74% | 48.63% |
| 9 | 30.0 | 72.0 | 39.64% | 68.85% | 77.91% | 81.16% | 82.41% | 74.20% |
| 10 | 30.0 | 54.0 | 43.00% | 60.57% | 66.98% | 68.99% | 71.99% | 65.30% |

-continued

Trial 1

| | amount of ai Spinetoram, g/ha | amount of ai Tau-fluvalinate, g/ha | Efficacy of control (%) | | | | | |
|---|---|---|---|---|---|---|---|---|
| | | | 1 DAA | 3 DAA | 5 DAA | 7 DAA | 10 DAA | 14 DAA |
| 11 | 30.0 | 36.0 | 19.18% | 48.80% | 58.37% | 58.26% | 65.28% | 55.02% |
| 12 | 30.0 | 18.0 | 38.30% | 35.95% | 49.77% | 42.90% | 57.18% | 45.89% |
| 13 | 15.0 | 72.0 | 52.72% | 71.46% | 75.81% | 66.67% | 72.92% | 63.24% |
| 14 | 15.0 | 54.0 | 49.36% | 61.87% | 65.12% | 55.36% | 64.81% | 55.71% |
| 15 | 15.0 | 36.0 | 43.33% | 54.03% | 50.47% | 57.10% | 57.87% | 39.04% |
| 16 | 15.0 | 18.0 | 24.14% | 45.53% | 35.81% | 42.32% | 53.47% | 38.81% |
| 17 | 60.0 | 0.0 | 68.61% | 72.98% | 66.28% | 54.78% | 56.25% | 48.17% |
| 18 | 0.0 | 72.0 | 67.81% | 66.01% | 68.84% | 60.87% | 64.81% | 36.76% |
| 19 | 15.0 | 0.0 | 51.31% | 57.52% | 53.49% | 40.87% | 40.05% | 36.30% |
| 20 | 0.0 | 18.0 | 36.42% | 29.41% | 40.23% | 25.22% | 39.81% | 38.58% |
| 21 | 45.0 | 0.0 | 53.92% | 59.69% | 58.84% | 43.48% | 46.30% | 34.25% |
| 22 | 0.0 | 54.0 | 56.54% | 62.53% | 59.30% | 46.38% | 51.39% | 37.21% |
| 23 | 30.0 | 0.0 | 51.71% | 51.42% | 50.47% | 37.68% | 42.82% | 28.77% |
| 24 | 0.0 | 36.0 | 46.28% | 55.34% | 55.35% | 44.64% | 42.13% | 26.94% |

Trial 2

| | amount of ai Spinetoram g/ha | amount of ai Tau-fluvalinate g/ha | Efficacy of control (%) | | | | |
|---|---|---|---|---|---|---|---|
| | | | 1 DAA | 3 DAA | 5 DAA | 10 DAA | 16 DAA |
| 1 | 60.0 | 72.0 | 95.81% | 96.26% | 93.61% | 96.23% | 42.74% |
| 2 | 60.0 | 54.0 | 90.35% | 89.69% | 89.23% | 91.21% | 43.79% |
| 3 | 60.0 | 36.0 | 74.85% | 79.28% | 73.49% | 79.39% | 32.88% |
| 4 | 60.0 | 18.0 | 55.65% | 51.00% | 53.73% | 64.33% | 27.64% |
| 5 | 45.0 | 72.0 | 95.13% | 92.30% | 94.79% | 94.87% | 41.90% |
| 6 | 45.0 | 54.0 | 79.14% | 81.09% | 78.22% | 82.11% | 40.64% |
| 7 | 45.0 | 36.0 | 62.38% | 66.14% | 60.83% | 67.57% | 37.08% |
| 8 | 45.0 | 18.0 | 46.00% | 49.04% | 46.51% | 53.56% | 28.27% |
| 9 | 30.0 | 72.0 | 79.59% | 80.86% | 79.64% | 80.65% | 38.76% |
| 10 | 30.0 | 54.0 | 73.20% | 77.69% | 74.44% | 79.71% | 38.13% |
| 11 | 30.0 | 36.0 | 48.15% | 52.32% | 53.73% | 61.19% | 33.30% |
| 12 | 30.0 | 18.0 | 42.20% | 44.17% | 48.40% | 53.45% | 30.16% |
| 13 | 15.0 | 72.0 | 66.28% | 65.23% | 61.42% | 59.73% | 35.19% |
| 14 | 15.0 | 54.0 | 61.70% | 60.36% | 52.66% | 57.11% | 30.58% |
| 15 | 15.0 | 36.0 | 46.59% | 50.06% | 40.36% | 44.04% | 41.06% |
| 16 | 15.0 | 18.0 | 30.12% | 31.60% | 28.28% | 33.58% | 30.37% |
| 17 | 60.0 | 0.0 | 71.25% | 73.84% | 72.66% | 77.41% | 35.61% |
| 18 | 0.0 | 72.0 | 43.18% | 53.34% | 51.48% | 55.86% | 33.93% |
| 19 | 15.0 | 0.0 | 23.20% | 38.17% | 37.16% | 42.05% | 41.06% |
| 20 | 0.0 | 18.0 | −0.88% | 20.16% | 14.44% | 22.70% | 23.44% |
| 21 | 45.0 | 0.0 | 60.82% | 57.87% | 62.72% | 66.84% | 29.11% |
| 22 | 0.0 | 54.0 | 31.58% | 43.37% | 45.56% | 48.54% | 30.37% |
| 23 | 30.0 | 0.0 | 51.27% | 46.21% | 53.49% | 56.80% | 26.38% |
| 24 | 0.0 | 36.0 | 19.59% | 39.75% | 32.43% | 38.91% | 33.72% |

Phytotoxicity

No symptoms were observed in any of the treatments of Examples 1-6.

CONCLUSIONS

The results show very good efficacy control over the pests with a combination of spinetoram and the co-component (Novaluron, Pyriproxyfen, Tau-fluvalinate). Additionally these combinations, afford very good control over more than one pest that tend to be present on the plant at the same time.

While this invention has been shown and described with reference to preferred embodiments thereof, it will be understood by those skilled in the art that many alternatives, modifications and variations may be made thereto without departing from the spirit and scope of the invention. Accordingly, it is intended to embrace all such alternatives, modifications, and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

What is claimed is:
1. A pesticidal mixture comprising:
 (a) spinetoram; and
 (b) a compound of group A selected from novaluron, pyriproxyfen, tau-fluvalinate, and a combination thereof,
 wherein a weight ratio of spinetoram to the compound of group A is from 1:10 to 10:1.

2. The pesticidal mixture according to claim 1 in a synergistic effective amount.

3. A pesticidal composition comprising the pesticidal mixture according to claim 1; and an agriculturally acceptable carrier.

4. The pesticidal composition according to claim 3 for use in controlling pests in a crop or a locus thereof.

5. A method for controlling pests in a crop, comprising:
applying a pesticidal combination to pests or a locus, where control of the pest is desired,
wherein the pesticidal combination comprises:
(a) spinetoram; and
(b) a compound of group A selected from novaluron, pyriproxyfen, tau-fluvalinate, and combination thereof, and
wherein a weight ratio of spinetoram to the compound of group A is from 1:10 to 10:1.

6. The method according to claim 5, wherein an application rate of spinetoram is from 1 g/ha to 500 g/ha.

7. The method according to claim 5, wherein an application rate of the compound of group A is from 1 g/ha to 500 g/ha.

8. The method according to claim 5, wherein an application rate of the pesticidal combination according to claim 5 is from 1 g/ha to 1000 g/ha.

9. The method according to claim 5, wherein spinetoram and the compound of group A are applied concomitantly or sequentially.

10. A kit comprising (a) at least one container including spinetoram; (b) at least one container including a compound of group A selected from novaluron, pyriproxyfen, tau-fluvalinate, and a combination thereof; and (c) instructions for applying a combination of said spinetoram and said compound of group A a pest or a locus, where control of the pest is desired, wherein a weight ratio of spinetoram to the compound of group A is from 1:10 to 10:1.

11. The kit of claim 10 wherein said spinetoram and said compound of group A are applied concomitantly or sequentially.

12. A kit comprising
(a) at least one container including (i) spinetoram; and (ii) a compound of group A selected from novaluron, pyriproxyfen, tau-fluvalinate, and a combination thereof; and
(b) instructions for applying said spinetoram and said compound of group A onto a pest or a locus, where control of the pest is desired, wherein a weight ratio of spinetoram to the compound of group A is from 1:10 to 10:1.

* * * * *